US010337962B2

(12) United States Patent
Stuart et al.

(10) Patent No.: US 10,337,962 B2
(45) Date of Patent: Jul. 2, 2019

(54) VISIBLE AUDIOVISUAL ANNOTATION OF INFRARED IMAGES USING A SEPARATE WIRELESS MOBILE DEVICE

(71) Applicant: Fluke Corporation, Everett, WA (US)

(72) Inventors: Michael D. Stuart, Issaquah, WA (US); Jordan Schlichting, Plymouth, MN (US); John Neeley, Seattle, WA (US)

(73) Assignee: Fluke Corporation, Everett, WA (US)

( * ) Notice: Subject to any disclaimer, the term of this patent is extended or adjusted under 35 U.S.C. 154(b) by 288 days.

(21) Appl. No.: 14/214,082

(22) Filed: Mar. 14, 2014

(65) Prior Publication Data

US 2014/0267765 A1    Sep. 18, 2014

Related U.S. Application Data

(60) Provisional application No. 61/801,380, filed on Mar. 15, 2013, provisional application No. 61/876,719, filed on Sep. 11, 2013.

(51) Int. Cl.
*H04N 5/232* (2006.01)
*G01M 99/00* (2011.01)
(Continued)

(52) U.S. Cl.
CPC .............. *G01M 99/00* (2013.01); *G01D 1/00* (2013.01); *G01D 7/00* (2013.01); *G01D 7/02* (2013.01);
(Continued)

(58) Field of Classification Search
CPC ........................................................ H04N 5/33
(Continued)

(56) References Cited

U.S. PATENT DOCUMENTS 5,386,117 A    1/1995  Piety
5,637,871 A    6/1997  Piety
(Continued)

FOREIGN PATENT DOCUMENTS

CA    2152024 A1    12/1995
CN    101339671 A    1/2009
(Continued)

OTHER PUBLICATIONS

Extech Instruments, "Extech EX540 Wireless Datalogging selected as 2010 EC&M Product of the Year Category Winner," Press Release, Mar. 18, 2009, 2 pages.
(Continued)

*Primary Examiner* — Jonathan R Messmore
(74) *Attorney, Agent, or Firm* — Seed Intellectual Property Law Group LLP

(57) ABSTRACT

A smart phone user captures video and still images of a motor and makes a sound recording of his observations. The images and recordings are tagged with a date/time stamp, a serial number, bar code, matrix code, RFID code, or geo-location and sent wirelessly to an infrared camera. The infrared camera has a collocation application that reads the tag and creates a folder which holds the infrared image and the auxiliary information from the smartphone related to an asset. The collocation program also adds icons to the infrared image. By operating the user interface (not shown) of the infrared camera, the user may select an icon to view the images and listen to the sound recording.

36 Claims, 6 Drawing Sheets

(51) Int. Cl.

| | | |
|---|---|---|
| *G06F 15/00* | (2006.01) | |
| *G08B 5/00* | (2006.01) | |
| *G06T 11/20* | (2006.01) | |
| *H04N 5/33* | (2006.01) | |
| *G01D 1/00* | (2006.01) | |
| *G01D 7/00* | (2006.01) | |
| *G06K 9/64* | (2006.01) | |
| *G01D 9/00* | (2006.01) | |
| *G06Q 20/08* | (2012.01) | |
| *G08C 17/02* | (2006.01) | |
| *H04Q 9/00* | (2006.01) | |
| *G01D 7/08* | (2006.01) | |
| *G01D 7/02* | (2006.01) | |
| *G16H 10/40* | (2018.01) | |

(52) U.S. Cl.
CPC .................. *G01D 7/08* (2013.01); *G01D 9/00* (2013.01); *G06F 15/00* (2013.01); *G06K 9/64* (2013.01); *G06Q 20/085* (2013.01); *G06Q 20/0855* (2013.01); *G06T 11/206* (2013.01); *G08B 5/00* (2013.01); *G08C 17/02* (2013.01); *G16H 10/40* (2018.01); *H04N 5/23229* (2013.01); *H04N 5/33* (2013.01); *H04Q 9/00* (2013.01); *H04Q 2209/40* (2013.01); *H04Q 2209/47* (2013.01); *H04Q 2209/50* (2013.01); *H04Q 2209/86* (2013.01); *H04Q 2209/883* (2013.01)

(58) Field of Classification Search
USPC ........................................................ 348/164
See application file for complete search history.

(56) References Cited

U.S. PATENT DOCUMENTS

| | | | |
|---|---|---|---|
| 5,664,207 A | | 9/1997 | Crumpler |
| 6,750,978 B1* | | 6/2004 | Marggraff ............ G06F 3/0481 235/375 |
| 7,076,239 B2 | | 7/2006 | Kirkup |
| 7,191,184 B2 | | 3/2007 | Laborde et al. |
| 7,304,618 B2 | | 12/2007 | Plathe |
| 7,454,050 B2 | | 11/2008 | Garvey |
| 7,478,305 B2 | | 1/2009 | Betawar |
| 7,528,372 B2 | | 5/2009 | Garvey, III |
| 7,561,200 B2 | | 7/2009 | Garvey, III |
| 7,703,032 B2 | | 4/2010 | Wells |
| 7,706,596 B2 | | 4/2010 | Garvey |
| 7,728,275 B2 | | 6/2010 | Blanchard |
| 7,902,507 B1 | | 3/2011 | Garvey, III |
| 7,995,830 B2 | | 8/2011 | Garvey |
| 8,003,942 B2 | | 8/2011 | Garvey, III |
| 8,059,882 B2 | | 11/2011 | Amidi |
| 8,119,986 B1 | | 2/2012 | Garvey, III |
| 8,124,923 B2 | | 2/2012 | Blanchard |
| 8,148,687 B1 | | 4/2012 | Praly |
| 8,300,922 B1 | | 10/2012 | Garvey, III |
| 8,334,513 B1 | | 12/2012 | Garvey, III |
| 8,358,903 B1 | | 1/2013 | Meads et al. |
| 8,368,001 B2 | | 2/2013 | Blanchard |
| 8,447,541 B2 | | 5/2013 | Rada et al. |
| 8,754,779 B2 | | 6/2014 | Ruther |
| 8,976,039 B2 | | 3/2015 | O'Hara et al. |
| 2001/0038343 A1 | | 11/2001 | Meyer |
| 2003/0184653 A1 | | 10/2003 | Ohkubo |
| 2004/0249605 A1 | | 12/2004 | Komatsu |
| 2005/0125512 A1 | | 6/2005 | Fuller, III |
| 2006/0071812 A1 | | 4/2006 | Mason, Jr. |
| 2007/0032244 A1 | | 2/2007 | Counts et al. |
| 2007/0118323 A1 | | 5/2007 | Ishizuka |
| 2008/0231719 A1 | | 9/2008 | Benson |
| 2008/0263150 A1* | | 10/2008 | Childers ............ H04L 41/0853 709/203 |
| 2009/0010484 A1* | | 1/2009 | Amidi ................ H04N 1/32101 382/100 |
| 2009/0100096 A1* | | 4/2009 | Erlichson ................ H04L 67/02 |
| 2009/0141593 A1 | | 6/2009 | Taha |
| 2010/0039516 A1 | | 2/2010 | Hollander et al. |
| 2010/0167659 A1 | | 7/2010 | Wagner |
| 2011/0099424 A1 | | 4/2011 | Rivera Trevino |
| 2011/0137678 A1 | | 6/2011 | Williams |
| 2011/0288810 A1 | | 11/2011 | Ishikawa |
| 2012/0004886 A1 | | 1/2012 | Jordil |
| 2012/0038760 A1 | | 2/2012 | Kantzes et al. |
| 2012/0047424 A1 | | 2/2012 | Rothschild |
| 2012/0130223 A1 | | 5/2012 | Reicher |
| 2012/0172023 A1 | | 7/2012 | Griff |
| 2012/0178438 A1 | | 7/2012 | Vashi |
| 2012/0223969 A1* | | 9/2012 | Schoeller ............ G06K 9/00664 345/633 |
| 2012/0224067 A1 | | 9/2012 | Stuart |
| 2012/0229270 A1 | | 9/2012 | Morley |
| 2012/0270505 A1 | | 10/2012 | Prakash |
| 2012/0300089 A1 | | 11/2012 | Sbaiz |
| 2012/0320189 A1 | | 12/2012 | Stuart |
| 2013/0009788 A1 | | 1/2013 | Langenberg |
| 2013/0029683 A1 | | 1/2013 | Kim |
| 2013/0065633 A1 | | 3/2013 | Sridhara |
| 2013/0066576 A1 | | 3/2013 | Cs |
| 2013/0124136 A1* | | 5/2013 | Neeley ................ G01R 31/2834 702/122 |
| 2013/0127904 A1 | | 5/2013 | Dove et al. |
| 2013/0181978 A1 | | 7/2013 | Tsukagoshi et al. |
| 2013/0265502 A1* | | 10/2013 | Huebner ................ A63F 13/06 348/789 |
| 2013/0307992 A1 | | 11/2013 | Erlandsson |
| 2014/0124120 A1* | | 5/2014 | Pham ...................... B32B 41/00 156/64 |
| 2014/0236468 A1* | | 8/2014 | Dave ..................... H04W 4/029 701/300 |
| 2014/0278259 A1 | | 9/2014 | Neeley et al. |

FOREIGN PATENT DOCUMENTS

| | | | |
|---|---|---|---|
| CN | 101582819 A | | 11/2009 |
| DE | 102009054000.8 | * | 11/2009 |
| EP | 1 965 316 A2 | | 9/2008 |
| EP | 1 965 316 A3 | | 5/2012 |
| JP | 2008-39656 A | | 2/2008 |
| JP | 2011-55489 A | | 3/2011 |
| JP | 2012-54987 A | | 3/2012 |
| KR | 10-2008-0112692 A | | 12/2006 |
| KR | 10-2012-0065540 A | | 6/2012 |
| KR | 10-2012-0077332 A | | 7/2012 |
| WO | 2010/046820 A1 | | 4/2010 |
| WO | 2013/020110 A2 | | 2/2013 |
| WO | 2013/020110 A3 | | 2/2013 |

OTHER PUBLICATIONS

Extech Instruments, "Extech EX845 METERLiNK™ Clamp Meter Transmit Readings to FLIR IR Cameras," Press Release, Apr. 1, 2010, 3 pages.

Extech Instruments, "MultiMeter/Datalogger with Wireless PC Interface," Product Datasheet, Jul. 14, 2011, 1 page.

Extech Instruments, "Wireless TRMS Multimeter—Model EX540," User's Guide, Apr. 1, 2010, 17 pages.

International Search Report and Written Opinion dated Sep. 12, 2014, in International Patent Application No. PCT/US2014/029867, filed Mar. 14, 2014, 12 pages.

International Search Report dated Jul. 10, 2014, in International Patent Application No. PCT/US2014/029561, filed Mar. 14, 2014, 2 pages.

International Search Report and Written Opinion dated Jul. 17, 2014, in International Patent Application No. PCT/US2014/029889, 13 pages.

International Search Report and Written Opinion dated Jul. 18, 2014, in International Patent Application No. PCT/US2014/029885, 16 pages.

(56) References Cited

OTHER PUBLICATIONS

International Search Report and Written Opinion dated Jul. 22, 2014, in International Patent Application No. PCT/US2014/029883, 13 pages.
International Search Report and Written Opinion dated Jul. 24, 2014, in International Patent Application No. PCT/US2014/029879, 12 pages.
Extended European Search Report, dated Sep. 30, 2016, for European Application No. 14765749.8-1952 / 2974266, 13 pages.
Extended European Search Report, dated Oct. 21, 2016, for European Application No. 14763237.6-1855 / 2972976, 9 pages.
Chinese First Office Action, dated Dec. 20, 2017, for Chinese Application No. 201480027601.X, 32 pages (with English Translation).
JP Notification of Rejection for JP Application No. 2016-503140 dated Mar. 27, 2018, 10 pgs.

* cited by examiner

VISIBLE AUDIOVISUAL ANNOTATION OF INFRARED IMAGES USING A SEPARATE WIRELESS MOBILE DEVICE

CROSS-REFERENCES TO RELATED APPLICATIONS

This application claims the benefit of Provisional Application No. 61/801,380, filed Mar. 15, 2013, and Provisional Application No. 61/876,719, filed Sep. 11, 2013, the disclosures of which are hereby incorporated by reference herein.

BACKGROUND

The present invention relates to the field of infrared cameras. More particularly, this invention relates to infrared cameras enabling an operator to capture a thermal image of an asset and the scene or area where the asset is located and then associate it with any auxiliary information relating to the asset or scene.

Thermal imaging cameras have long been used in many settings to measure temperature profiles and analyze thermal variations and differences of one or more assets in a scene such as an electric motor in an area of a manufacturing plant. To that end, such profiles can be used in comparing the different temperatures of the assets at any given time, or conversely, can be used in comparing these temperatures or thermal variations and differences over a period of time. For example, infrared cameras are frequently used in industrial applications as part of preventative maintenance programs and for building sciences and diagnostics inspections. These types of programs often typically rely on periodic inspections of the assets of a plant, facility, or structure to discover likely failures before they occur or monitor and document ongoing performance. For example, in an industrial setting, plant personnel often develop survey routes in order to routinely gather temperature data on the identified equipment. As is known, similar examples exist in other applications for building sciences as well.

In an industrial setting example, after collecting a thermal baseline image for each piece of equipment along a route, a person (such as a thermographer, an inspector, a building performance professional, an electrician, a technician, etc.) can then identify changes in thermal characteristics over the course of several inspections by comparing later thermal images of the equipment with the baseline image or other prior images. Changes in thermal characteristics can in some cases indicate the imminent failure of a part, thus allowing the person to schedule maintenance or replacement prior to failure.

In a simple case, a person can visually compare thermal images captured at different times to determine changes in thermal characteristics over the time period. However, only so much information can be gleaned solely from thermal images. To aid in the analysis of a most recent image captured or in comparing that image to images previously captured, infrared imaging cameras have been configured to allow operators to add notes or annotations to an image. These annotations are generally created as audio or text files, and can be subsequently saved to the image in order to provide supplementary information that is difficult to ascertain from the image alone.

However, issues were encountered in adding these annotations to the image. In particular, some cameras only enable annotations to be added at the time the thermal image is saved (with limited ability for later modification), while other cameras enable annotations to be added after the image is saved. As such, it is not uncommon to find operators of these cameras further carrying a notebook to jot down their impressions of the scene in the field. In turn, the operator waits until later to combine these impressions into a single file which can then be stored with the saved image of the scene. Unfortunately, this process is time-consuming and invites error, because what is observed and noted in the field may not be fully recalled, even with the use of such notebook. Further, the operator may not be able to remember the particular image that the annotations correspond to, inviting further potential error.

Many of the above and other problems are solved by embodiments of an apparatus and methods shown in U.S. Pat. No. 9,176,990, assigned to the assignee of this patent and hereby incorporated by reference. The '990 patent shows a thermal imager for capturing a primary thermal image of an asset or scene and then associating it, as desired, with auxiliary information relating to the asset or scene. The auxiliary information can be associated with the primary thermal image in the field after the image is captured. The auxiliary information can pertain to further detail regarding the asset, the surroundings of the scene, and/or the surroundings of the location of the scene, which when associated with the primary thermal image, collectively represents a form of asset information card for the image. The auxiliary information is generally in the form of images and video recordings, whether infrared and/or visible light, and can be associated to the primary thermal image in varying or distinct manners, such as being based on relatedness of the information to the asset or the scene. The infrared image is annotated with the other images and recordings in the thermal imager at or proximate the time of recording.

The infrared imager of the '990 patent has the added ability to capture still images, sound recordings, and video, and thereby annotate the infrared images by capturing the infrared images and the annotations at approximately the same time. However, many users continue to use their existing infrared imagers that have no ability to capture still and video images and sound recordings. As such, there remains a problem with annotating thermal images with other images and recordings taken by video camera, still image cameras, and sound recorders. Moreover, often the infrared images reside on a remote server and only require annotations with images and recording that can be captured by non-infrared equipment such as the ubiquitous smartphone which records video, audio, and still images. There remains a long felt and unmet need for such annotating infrared images with auxiliary information captured by non-infrared devices.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention described and claimed herein has a number of embodiments and should not be interpreted or otherwise limited to the abbreviated discussion of some embodiments in this summary. The embodiments of the invention address the problem of how to collocate (group) information about an asset, such as a motor or machine, by using tags. A primary piece of information is a thermal image. The thermal image is annotated with auxiliary information, including and not limited to digital images (still), sound recordings of notes spoken by an observer of the asset, and video images. Auxiliary information is captured with a smartphone, a digital camera, a digital recorder or a digital video camera. Each capture device applies a tag to the captured information that relates the captured information to an asset.

There are numerous types of tags, including date/time stamps, serial numbers, bar and matrix codes, RFID codes and geolocations (latitude and longitude) tags. The tagged information is processed in the capture device or is sent to another device where tags on the information are used to collocate information about the same asset into a common folder. The receiving device annotates a thermal image with icons that represent the types of auxiliary information in the folder.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Figure 1:
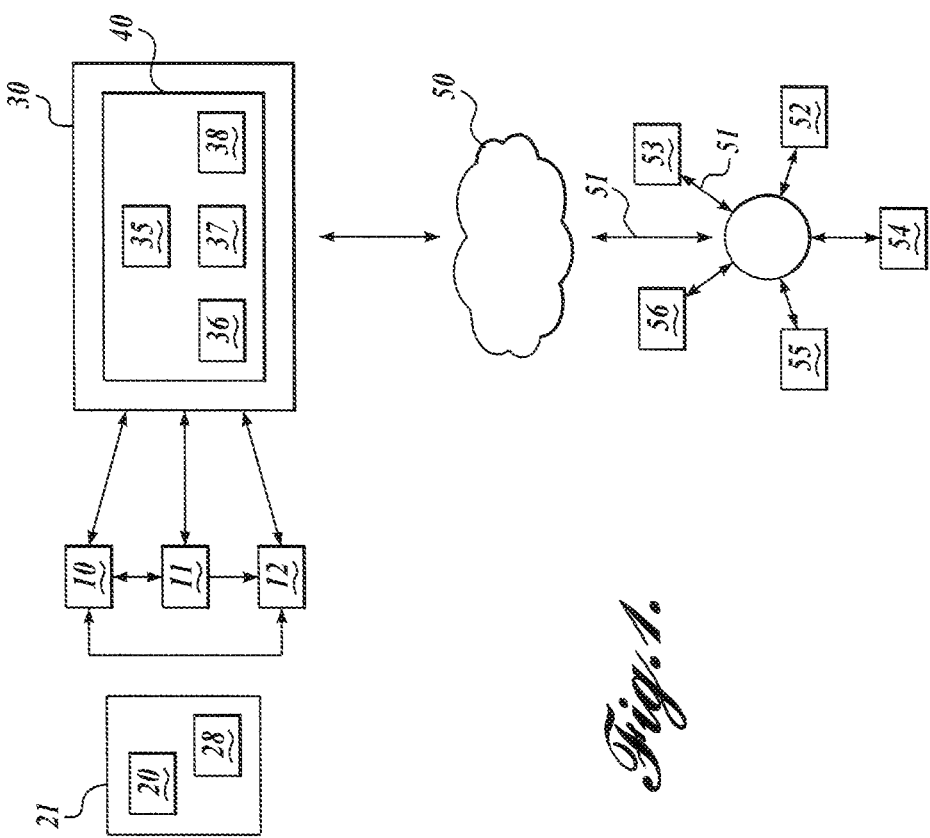
FIG. 1 is a general schematic diagram of an embodiment of an annotation system.

Turning to FIG. 1, a system 100 is shown. One or more capture devices 10-12 capture infrared images, still images, video images and sound recordings of assets 20, such as electric motors and their surrounding area or related environment 21. The asset 20 and its surrounding area (scene) 21 are labeled with a tag 28. Tags 28 are indicia or codes that relate captured information to an asset. Capture devices 10-12 capture thermal images, auxiliary information and their respective tag information. The capture devices 10-12 also apply one or more tags to captured information so that each thermal image 35 and auxiliary information have one or more tags 28 and each tag is related to the same asset 20. The capture devices 10-12 have wireless transceivers for sending infrared images 35 and captured auxiliary information and their tags to an annotation/storage/display (ASD) device 30. The ASD 30 is adapted to send asset folders 40 to a cloud storage device 50 from which annotated thermal images of an asset may be distributed to multiple devices 53-56 via wired or wireless connections 51 and the internet 52.

The ASD 30 may be a personal computer, a tablet computer, or a server. The ASD 30 has a processor 31 and a collocation program 33. The processor 31 operates the collocation program 33 to sort thermal images and auxiliary information with related tags into a common folder 40 to provide a folder having the infrared image 35 and auxiliary information. The processor also operates the collocation program to create icons 36-38 representative of the types of auxiliary information associated with the tag. Icons 36-38 are symbols representative of visual images 6, sound recordings 7, and video images 8, respectively.

Figure 2:
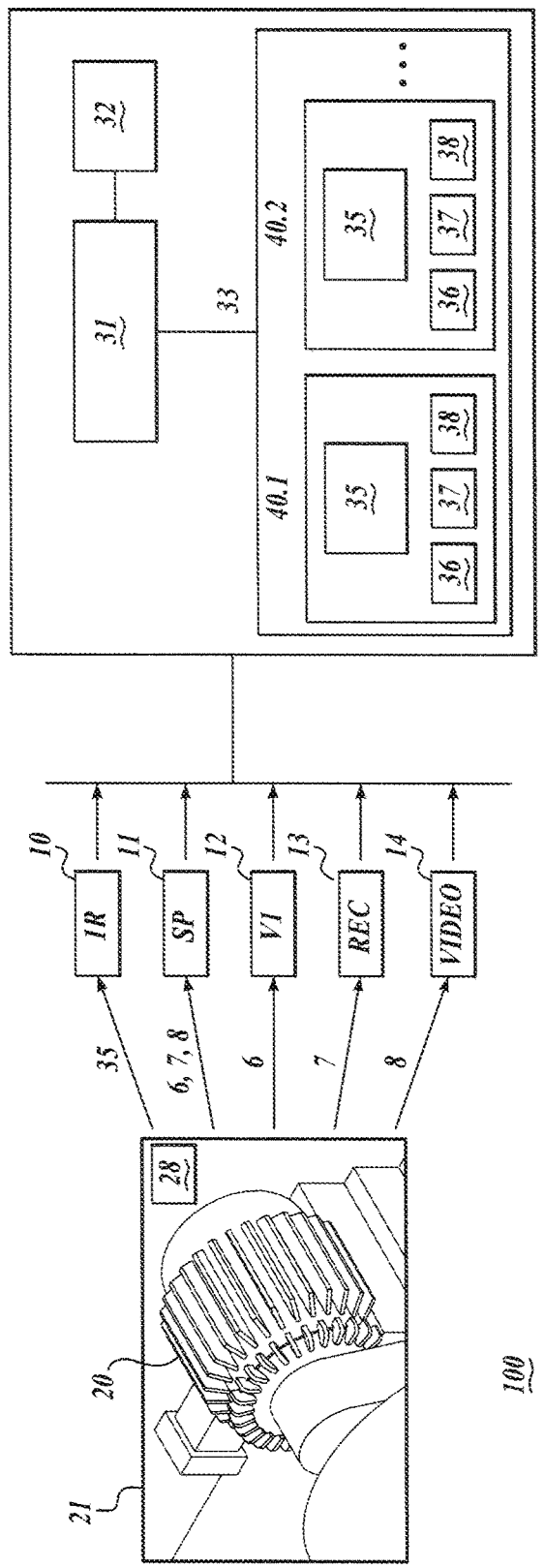
FIG. 2 is a more detailed general schematic diagram of an embodiment of an annotation system.

Moving to FIG. 2, there is a more detailed view of system 100. An asset 20, such as a motor 20, is shown in an area 21. The capture devices include an infrared camera 10 capable of capturing an infrared image 35 of the motor 20 or other asset. A smartphone 11 is a versatile capture device and captures video images 8, sound recordings 7, and still images 6. The smartphone 11 also captures different types of tags including, and not limited to, serial numbers, bar codes or matrix codes, date/time stamps for images, and audio recordings. Other tag embodiments include geolocation information (latitude and longitude) using global positioning circuitry and GPS programs that provide latitude and longitude values for the location of an asset 20. Still further tag embodiments include RFID tags. Smartphones may be equipped with circuitry and programs for reading all such codes.

Other capture devices 12-14 include suitable apparatus and circuitry to apply one or more tags to captured auxiliary information including images 6, sound recordings 7, and videos 8. The digital camera 12 and video camera 14 can apply date/time stamps to information and are inherently capable of capturing images of a serial number, bar code, or matrix (two-dimensional) code, which can be later deciphered as tags for asset 20. The digital recorder 13 may also attach a date/time stamp to a recording and the user may make an audible record of a serial number that can also be deciphered later. The other capture devices 12-14 may also be equipped with or modified to include apparatus and circuitry to detecting and appending RFID and geolocation codes to auxiliary information. Each capture device may send its information via a wired or wireless communication path to the ASD 30.

The ASD 30 has a processor 31, a memory 32, and one or more computer programs 33 for collocating images. Memory 32 holds multiple folders 40.1, 40.2, 40.3, 40.N of thermal images and auxiliary information. Each folder 40.N has an infrared image 35 of an asset 20 and the thermal image is annotated with icons 36-38 representing the types of auxiliary information in the folder. ASD 30 has suitable apparatus, methods and computer programs, such as optical character recognition and speech recognition programs, to decipher and recognize serial numbers, bar codes, matrix codes and audible notes corresponding to tags. The tag identification programs may operate independently or together to collocate received images and recordings. For example, audio recordings of spoken serial numbers are recognized by speech recognition programs. Such audio recordings may be processed together with the date/time tag data to collocate the audio recording with a captured image having similar date/times.

ASD 30 has a display 34 for displaying an infrared image 35 of the motor 20 or other asset with one or more icons 36, 37, 38 on the bottom of image 35. The icons 36-38 refer to still images, audio recordings, and video images, respectively, of the motor 20 and its relevant area or environment 21. A user operating an input device 30 may access any folder 40.N and display it on display 34. By clicking one of icons 36-38, the user may display still or video images or listen to comments in the audio annotations. The input device 39 is any suitable device and includes one or more of a keyboard, mouse, track ball, track pad, and touch screen on the display 34 and combinations thereof.

Figure 3:
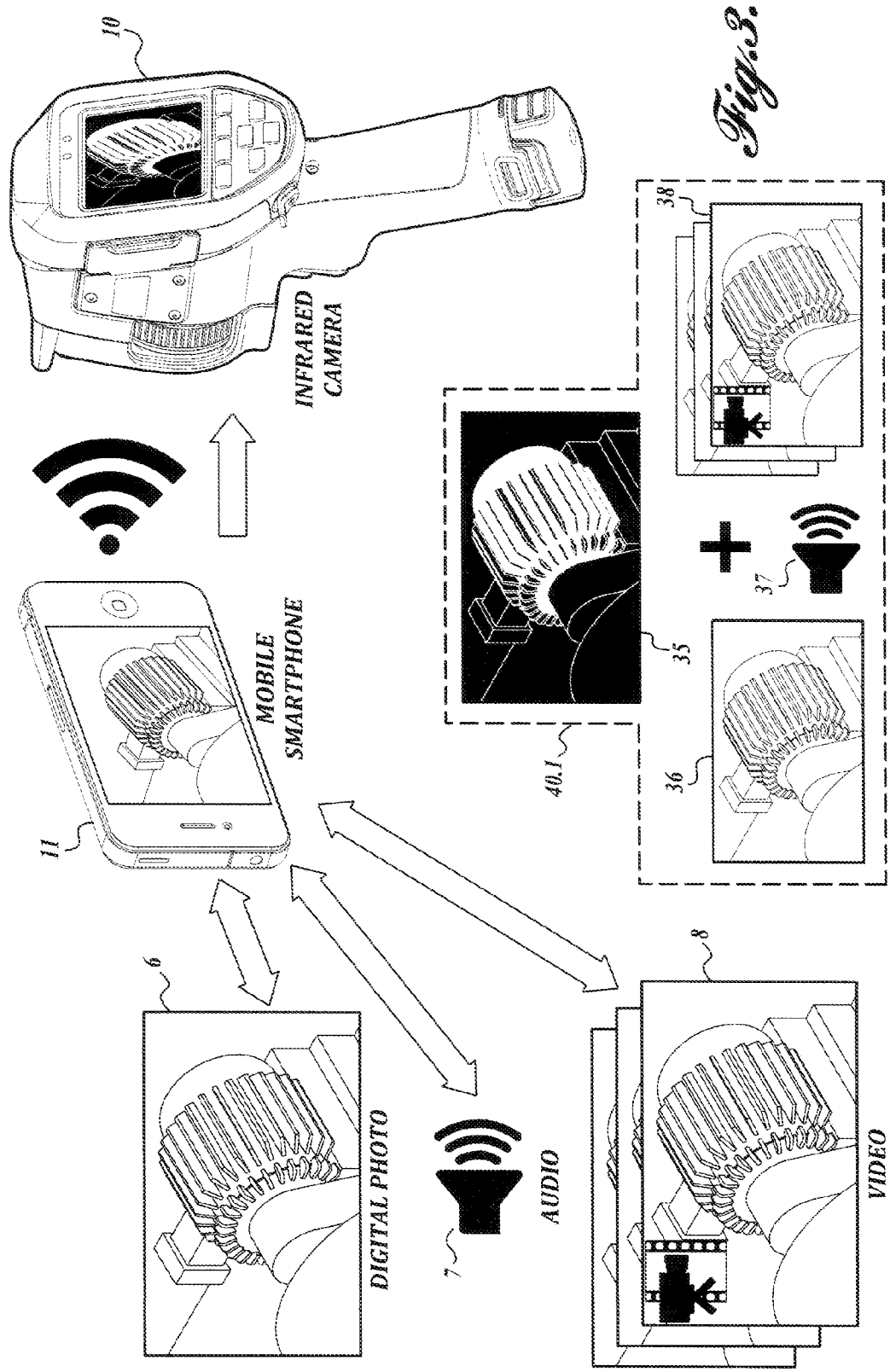
FIG. 3 is a schematic block diagram of a first specific embodiment of an annotation system.

FIG. 3 shows a first specific embodiment. The user operates an infrared camera 10 to capture a thermal image of a motor 20. The user then operates a smart phone 11 to capture video and still images of motor 20 and make a sound recording of his observations. The images and recordings are tagged with a date/time stamp and sent wirelessly to the infrared camera 10. The infrared camera 10 has a collocation application that reads the date/time stamps of the thermal, still and video images and the sound recording and creates a folder 40.1 that holds the infrared image 35 and the auxiliary information from the smartphone 11 related to asset 20. The collocation program also adds icons 36-38 to the infrared image 35. By operating the user interface (not shown) of the infrared camera 10, the user may select an icon 36-38 to view the images 6, 8 and listen to the sound recording 7.

The specific embodiment of FIG. 3 may be modified to substitute a digital video camera 14, a digital still image camera 12, or a digital recorder 13 for the smart phone 11. Each of the cameras 14, 12 and the recorder 13 has a wireless transmitter for sending images or recordings to infrared camera 10. The infrared camera 10 may capture or already have thermal image 35 with one or more tags including a serial number, barcode or matrix code data, a date/time stamp tag, a geolocation tag or an RFID tag. The devices 12-14 have one or more apparatus, circuitry, processor and supporting programs to acquire one or more tags, including and not limited to a serial number, barcode or matrix code data, a date/time stamp tag, a geolocation tag, or an RFID tag. The devices 12-14 append one or more tags to their respective images or recordings for transmission to the infrared camera 10. The infrared camera 10 has a collocation application that creates a folder 40.1 that has an infrared image 35 of the motor 20. The camera 10 and its collocation program reads the tags received from the devices 12-14, places the received images and recordings in the folder 40.1, and adds icons 36-38 to image 35. By operating the user interface (not shown) of the infrared camera 10, the user may select an icon 36-38 to view the images 6, 8 and listen to the sound recording 7.

Figure 4:
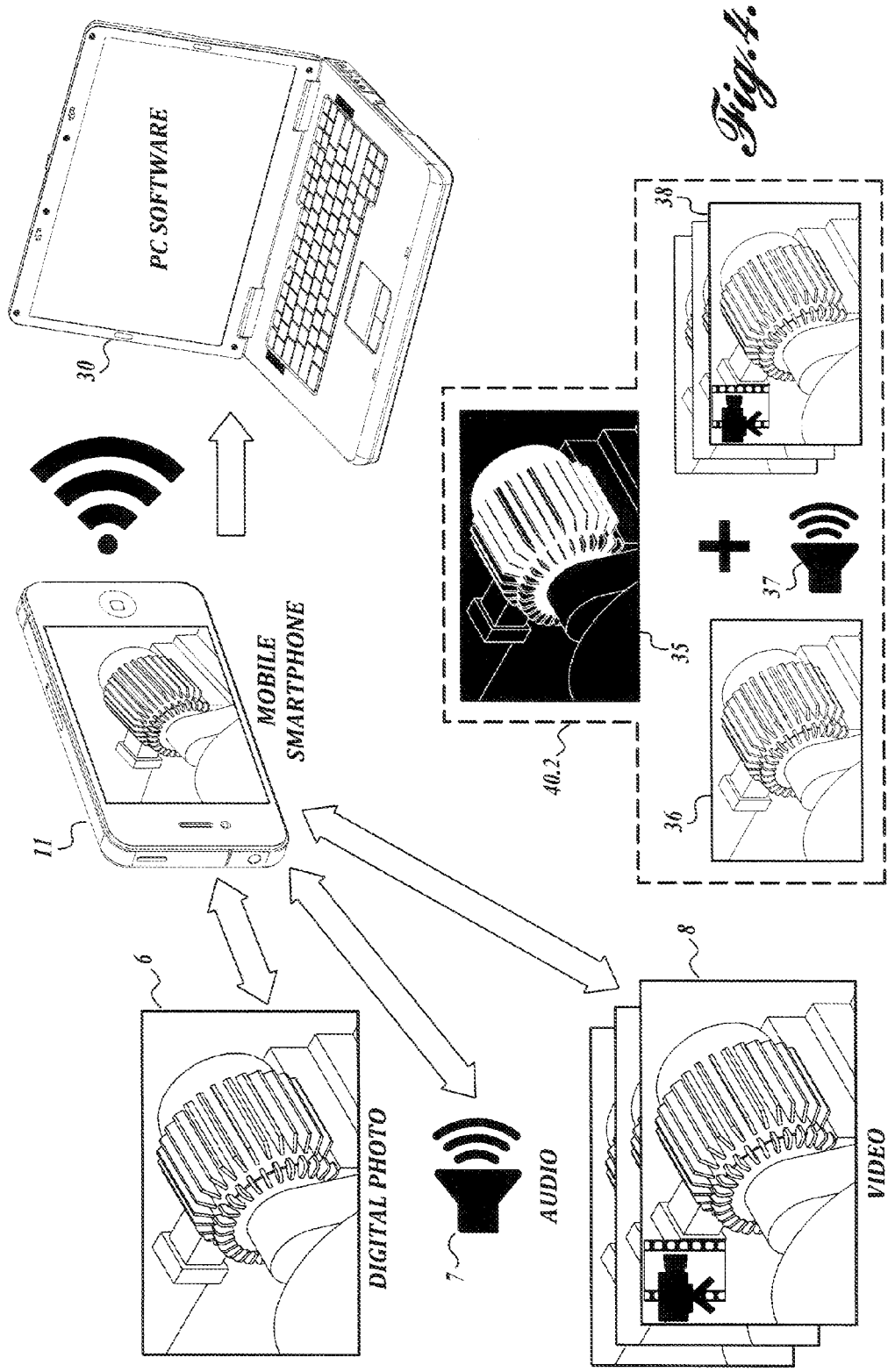
FIG. 4 is a schematic block diagram of a second specific embodiment of an annotation system.

FIG. 4 shows a second specific embodiment. The user operates a smart phone 11 to capture video and still images of motor 20 and make a sound recording of his observations. The smartphone has a global positioning apparatus and program for tagging images and sound recordings with the latitude and longitude of where the image and recordings were made. The smartphone 11 wirelessly sends the image and sound recording to a remote ASD (personal computer/database) 30. The ASD 30 holds a thermal image 35 of the motor in a folder 40.2. The image was taken last week. The ASD 30 has a collocation application that reads the geolocation tag of the images and recording received from the smartphone 11 and collocates the received images and recordings in folder 40.2, which has the same geolocations tag as the still and video images and the sound recording. Upon accessing folder 40.2, the user sees an infrared image 35 of the motor 20 and icons 36-38. By operating the user interface (not shown) of the smartphone 11, the user may select an icon 36-38 to view the images 6, 8 and listen to the sound recording 7.

Figure 5:
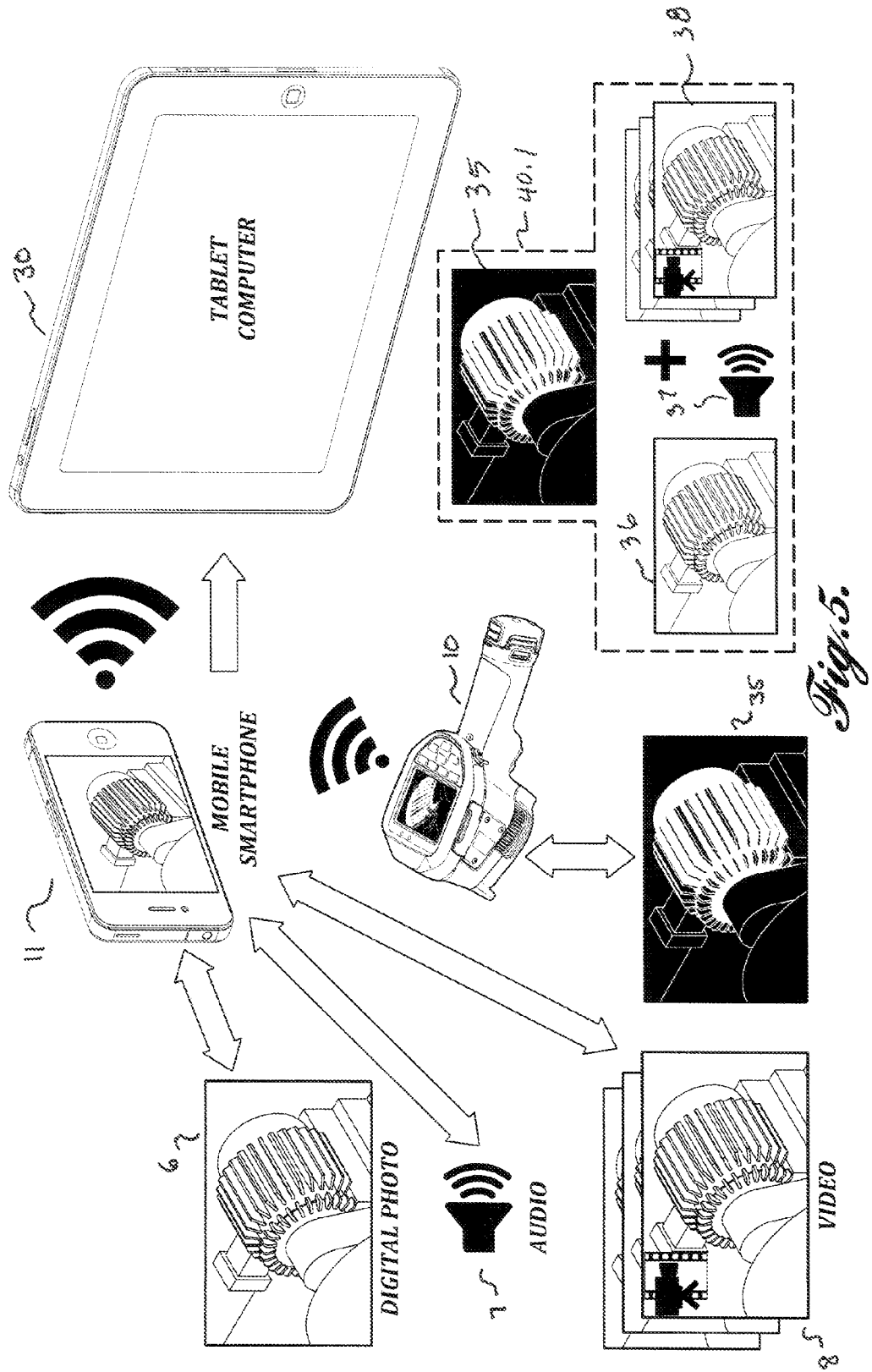
FIG. 5 is a schematic block diagram of a third specific embodiment of an annotation system.

FIG. 5 shows a third specific embodiment. The user operates a smart phone 11 to capture video and still images of motor 20 and make a sound recording of his observations. The smartphone attaches a date/time stamp tag to the images and recordings and wirelessly sends them to a tablet computer/ASD 30. A few minutes later, the user operates an infrared camera 10 to capture an infrared image 35 of the motor 20. The user sends the infrared image 35 with a date/time tag to the tablet computer/ASD 30. By operating the user interface (not shown) of the tablet, the user may select an icon 36-38 to view the images 6, 8 and listen to the sound recording 7.

The tablet computer/ASD 30 wirelessly receives the images and sound recordings from the infrared camera 10 and the smartphone 11. The tablet computer receives the thermal image 35 and stores it in a folder 40.3. The ASD 30 has a collocation application that reads the date/time stamp of the images and recordings received from the smartphone 11 and collocates those images and sound recording into folder 40.3 and adds icons 36-38 to the thermal images 35. The collocation program matches the images and sound recordings from the smartphone 11 to the thermal image 35 because they have date/time tags of the same day and close to the same time as the thermal image 35. In some embodiments, the collocation program may ask the user to accept or decline the prospective collocation of images and sound recordings with a given thermal image. Upon accessing folder 40.3, the user sees a thermal image 35 of the motor 20 and icons 36-38. By operating a user interface (not shown) of ASD 30, the user may select an icon and view the images 36, 37 and listen to the sound recording 38.

Figure 6:
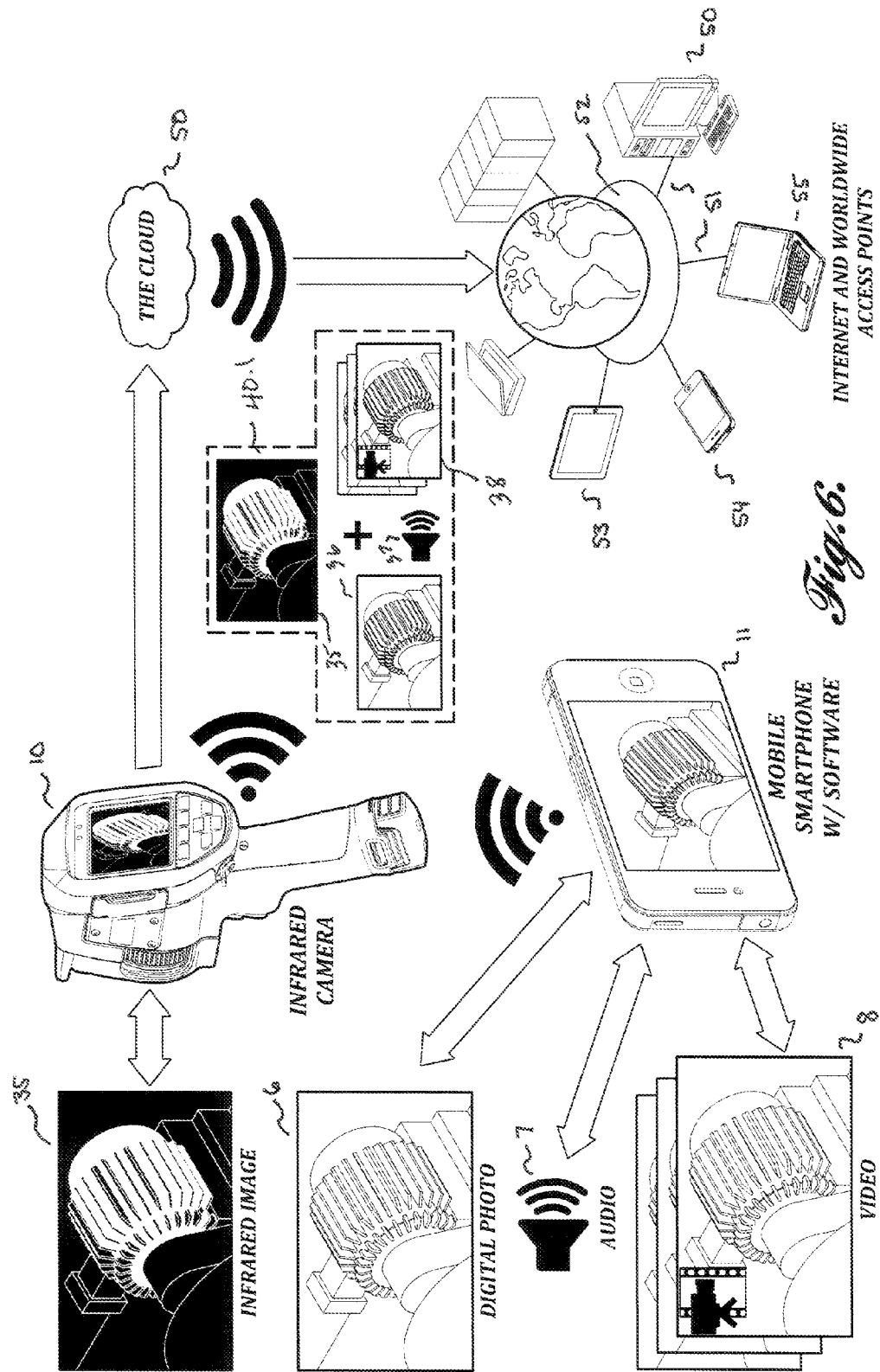
FIG. 6 is a schematic block diagram of a fourth specific embodiment of an annotation system.

FIG. 6 shows a fourth specific embodiment. The user operates an infrared camera 10 to capture a thermal image 35 of the motor 20 or other asset. Infrared camera 10 has a built-in barcode reader, not shown. It reads a barcode 5 disposed on the motor 20 or in close proximity to the motor, appends the barcode data to the thermal image as a tag, and stores the thermal image 35 and barcode data in a folder 40.4. The user then operates a smartphone 11 to capture still images, video images, and a sound recording of observations regarding motor 20. The smartphone 11 also captures images of the barcode 5 and allows the user to append the barcode image to the still and video images and to the sound recording. The images and sound recording are wirelessly sent to the infrared camera 10 that has a memory and a collocation application program. The collocation program identifies the barcode data and stores the thermal image 35 of the motor in folder 40.4. The collocation program also identifies the barcode tag data of the images and sound recording and stores the images and sound recording in folder 40.4 because each has the same tag information as the thermal image 35. The collocation program adds icons 36-38 to the thermal image 35 and wirelessly sends the annotated folder 40.4 to a cloud storage facility 50 where it may be downloaded to one or more devices 53-56 via wired or wireless connections 51 and the internet 52. Devices 53-56 may be infrared cameras, smartphones, tablet computers, personal computers, or other apparatus capable of displaying thermal images with icons that can be opened to their underlying images and recordings. By operating the user interface of the devices 53-56, the user may select an icon 36-38 to view the still and video images 6, 8 and listen to the sound recording 7.

While some embodiments of the invention have been shown and described, modifications and variations may be made thereto by those of ordinary skill in the art without departing from the spirit and scope of the present invention. For example, each of the capture devices 10-14 may be constructed or modified to have a collocation program and other programs for deciphering bar codes embedded in images and recognizing spoken serial numbers in sound recordings. Each of the capture devices may send its information to any of the other devices or to a personal computer, tablet computer, or cloud storage facility. In this regard, the personal computer, tablet computer, and cloud storage facility may have apparatus, circuitry, and programs for collocating tagged information into folders and for deciphering codes embedded in images and recordings.

It should be understood that aspects of the various embodiments may be interchanged either in whole or in part. Furthermore, those of ordinary skill in the art will appreciate that the foregoing description is by way of example only, and is not intended to limit the invention, except as further described in the appended claims. Those skilled in the art will understand that other and equivalent components and steps may be used to achieve substantially the same results in substantially the same way as that described and claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for annotating an infrared image, comprising:
    storing in a folder an infrared image of an asset captured by an infrared device that is not able to capture visible light still and video images and sound recordings, wherein the infrared image is stored in the folder with one or more tags associated with the asset;
    receiving auxiliary information from a non-infrared device that is separate from the infrared device, wherein the auxiliary information has at least one tag corresponding to a tag associated with the asset, and wherein the auxiliary information is at least one of a visible light still or video image, or a sound recording;
    operating a collocation program that sorts the auxiliary information received from the separate non-infrared device and, based on the at least one tag, stores the auxiliary information in the same folder with the infrared image;
    generating an annotated infrared image by adding the infrared image one or more icons representative of types of the auxiliary information stored in the folder, wherein the one or more icons are symbols representative of still images, sound recordings, and video images, respectively;
    storing the annotated infrared image; and
    displaying to a user the annotated infrared image of the asset annotated with the one or more icons representative of the types of the auxiliary information stored in the folder.

2. The method of claim 1, further comprising wirelessly receiving the auxiliary information from the non-infrared device.

3. The method of claim 1, wherein each still or video image or sound recording has at least one tag corresponding to a tag associated with the asset.

4. The method of claim 1, further comprising receiving user-selection of an icon in the annotated infrared image, the icon representing a type of auxiliary information stored in the folder, and in response to said user-selection of the icon, further providing to the user auxiliary information represented by the selected icon.

5. The method of claim 1, wherein a tag comprises information representative of an identity of the asset.

6. The method of claim 1, wherein a tag comprises a coded image.

7. The method of claim 6, wherein the tag comprises a serial number, a barcode, or a matrix code.

8. The method of claim 1, wherein a tag comprises a date/time stamp of when the infrared image or the still or video image or sound recording was captured.

9. The method of claim 1, wherein a tag comprises a geolocation code corresponding to a geographic location of the asset.

10. The method of claim 1, wherein the icons are representative of one or more of a group consisting of still images, video images, or sound recordings stored as auxiliary information in the folder.

11. The method of claim 1, further comprising capturing one or more of a group comprising still images, video images, and sound recordings, wherein each still or video image or sound recording is stored with at least one tag corresponding to a tag associated with the asset.

12. The method of claim 1, further comprising capturing the infrared image of the asset with an infrared camera.

13. The method of claim 1, further comprising capturing a still image, a video image, or a sound recording with a smartphone and wirelessly transmitting the captured still or video images or sound recording for storage as auxiliary information in the folder holding the infrared image.

14. The method of claim 1, further comprising storing the annotated infrared image in an infrared camera.

15. The method of claim 1, further comprising storing the annotated infrared image in a smartphone.

16. The method of claim 1, further comprising storing the annotated infrared image in a computer.

17. The method of claim 16, wherein the computer comprises a personal computer or a tablet computer.

18. The method of claim 1, further comprising storing the annotated infrared image in a computer cloud storage.

19. A system for annotating an infrared image, comprising:
    a storage apparatus that stores in a folder an infrared image of an asset captured by an infrared camera, wherein the infrared image is stored in the folder with one or more tags associated with the asset;
    a non-infrared device that captures auxiliary information and at least one tag associated with the asset, wherein the auxiliary information is at least one of a still image, a sound recording, or a video image, and wherein the non-infrared device is separate from the infrared camera and the storage apparatus and wirelessly transmits the auxiliary information and the at least one tag to the storage apparatus;
    a collocation program that sorts the auxiliary information into the folder corresponding to the at least one tag associated with the asset, and annotates the infrared image in the folder by adding to the infrared image one or more icons representative of the types of the auxiliary information stored in the folder, thus generating an annotated infrared image, wherein the one or more icons are symbols representative of still images, sound recordings, and video images, respectively;
    a processor in the storage apparatus that operates the collocation program to store the auxiliary information in the folder and to add the one or more icons to the infrared image in the folder to generate the annotated infrared image; and
    a display that displays the annotated infrared image of the asset.

20. The system of claim 19, wherein a tag comprises information representative of an identity of the asset.

21. The system of claim 19, wherein a tag comprises a coded image.

22. The system of claim 21, wherein the tag comprises a serial number, a barcode, or a matrix code.

23. The system of claim 19, wherein a tag comprises a date/time stamp of when the infrared image was captured.

24. The system of claim 19, wherein a tag comprises a geolocation code corresponding to a geographic location of the asset.

25. The system of claim 19, wherein the non-infrared device that captures the auxiliary information comprises one or more of a group consisting of a still image camera, a video camera, and a sound recorder that captures one or more of a group comprising still images, video images, and sound recordings associated with the asset.

26. The system of claim 19, wherein the storage apparatus comprises an infrared camera that captures the infrared image of the asset.

27. The system of claim 19, wherein the storage apparatus is one or more of a group consisting of a smartphone, a computer cloud storage, a personal computer, a tablet computer, a video camera, a digital camera, and a digital recorder.

28. An apparatus for annotating an infrared image comprising:
an input that receives wirelessly transmitted auxiliary information from a non-infrared device that is separate from the apparatus, wherein the auxiliary information is at least one of a still image, a sound recording, or a video image, and wherein the auxiliary information is associated with one or more tags;
a memory that stores in a folder an infrared image of an asset, the infrared image being captured by an infrared camera that is not able to capture said auxiliary information and is housed separate from the non-infrared device, wherein the infrared image is associated with one or more tags;
a collocation program that sorts the auxiliary information into folders according to the one or more tags associated with the auxiliary information, including sorting auxiliary information having one or more tags that correspond to the one or more tags associated with the asset into the folder storing the infrared image of the asset, wherein the collocation program further annotates the infrared image stored in the folder by adding to the infrared image one or more icons representative of the types of the auxiliary information stored in the folder, thus generating an annotated infrared image, wherein the one or more icons are symbols representative of still images, sound recordings, and video images, respectively;
a processor that operates the collocation program to store the auxiliary information in folders having infrared images with tags corresponding to the one or more tags of the auxiliary information, and to add the one or more icons to the infrared images representative of the types of auxiliary information stored in the respective folders to generate annotated infrared images; and
a display that displays the annotated infrared image of the asset.

29. The apparatus of claim 28, wherein said apparatus is an infrared camera.

30. The apparatus of claim 28, wherein a tag comprises information representative of an identity of the asset.

31. The apparatus of claim 28, wherein a tag comprises a coded image.

32. The apparatus of claim 31, wherein the tag comprises a serial number, a barcode, or a matrix code.

33. The apparatus of claim 28, wherein a tag comprises a date/time stamp of when the infrared image was captured.

34. The apparatus of claim 28, wherein a tag comprises a geolocation code corresponding to a geographic location of the asset.

35. The apparatus of claim 28, wherein the auxiliary information is wirelessly received from one or more non-infrared devices of a group consisting of a still image camera, a video camera, and a sound recorder that captures one or more of a group comprising still images, video images, and sound recordings.

36. The apparatus of claim 28, wherein the apparatus is one or more of a group consisting of a smartphone, a computer cloud storage, a personal computer, a tablet computer, a video camera, a digital camera, and a digital recorder.

* * * * *